_United States Patent_ [19]

Flockenhaus et al.

[11] 4,318,997
[45] Mar. 9, 1982

[54] PROCESS AND APPARATUS FOR MULTI-STAGE CATALYTIC METHANIZATION OF GASES

[75] Inventors: Claus Flockenhaus; Erich Hackler, Essen-Kettwig, both of Fed. Rep. of Germany

[73] Assignees: Thyssengas GmbH, Duisburg-Hamborn; Didier Engineering GmbH, Essen, both of Fed. Rep. of Germany

[21] Appl. No.: 148,150

[22] Filed: May 9, 1980

Related U.S. Application Data

[63] Continuation of Ser. No. 946,170, Sep. 27, 1978, abandoned.

[30] Foreign Application Priority Data

Oct. 22, 1977 [DE] Fed. Rep. of Germany ....... 2747517

[51] Int. Cl.$^3$ .............................................. C07C 1/04
[52] U.S. Cl. .................................. 518/704; 518/706; 518/728
[58] Field of Search ...... 260/449 M, 449 R, 449.6 M, 260/449.6 R; 48/197 R; 518/704, 706, 728

[56] References Cited

U.S. PATENT DOCUMENTS

| | | | |
|---|---|---|---|
| 3,511,624 | 5/1970 | Humphries et al. | 48/197 R |
| 3,888,043 | 6/1975 | Child et al. | 260/449 M X |
| 3,928,000 | 12/1975 | Child et al. | 48/197 R |
| 3,933,446 | 1/1976 | Timmins | 260/449 M |
| 3,938,968 | 2/1976 | White et al. | 260/449 M |
| 3,954,424 | 5/1976 | Goeke et al. | 48/197 R |

FOREIGN PATENT DOCUMENTS

1152009  5/1969  United Kingdom ........... 260/449 M

_Primary Examiner_—Howard T. Mars
_Attorney, Agent, or Firm_—Toren, McGeady & Stanger

[57] ABSTRACT

A process for the multi-stage catalytic methanization of a carbon monoxide-containing and hydrogen-containing feed gas at high pressure and temperature is carried out in three stages. In the first stage the feed gas is premethanized at a temperature of from 400° to 500° C.; in a second stage the premethanized gas is converted and in a third stage the converted gas is finally methanized at a temperature of from 300° to 380° C. Apparatus for carrying out this process preferably comprises a single elongated pressure reactor which is divided into three reaction zones each of which contains a reaction catalyst formed into a fluidized bed. The feed gas preferably flows upwards through the reactor firstly through the first fluidized bed, then through the second fluidized bed and finally through the third fluidized bed after which the product gas is withdrawn from the top of the reactor. The reactions takes place isothermally and for this purpose each of the zones is preferably provided with an independent cooling system.

6 Claims, 1 Drawing Figure

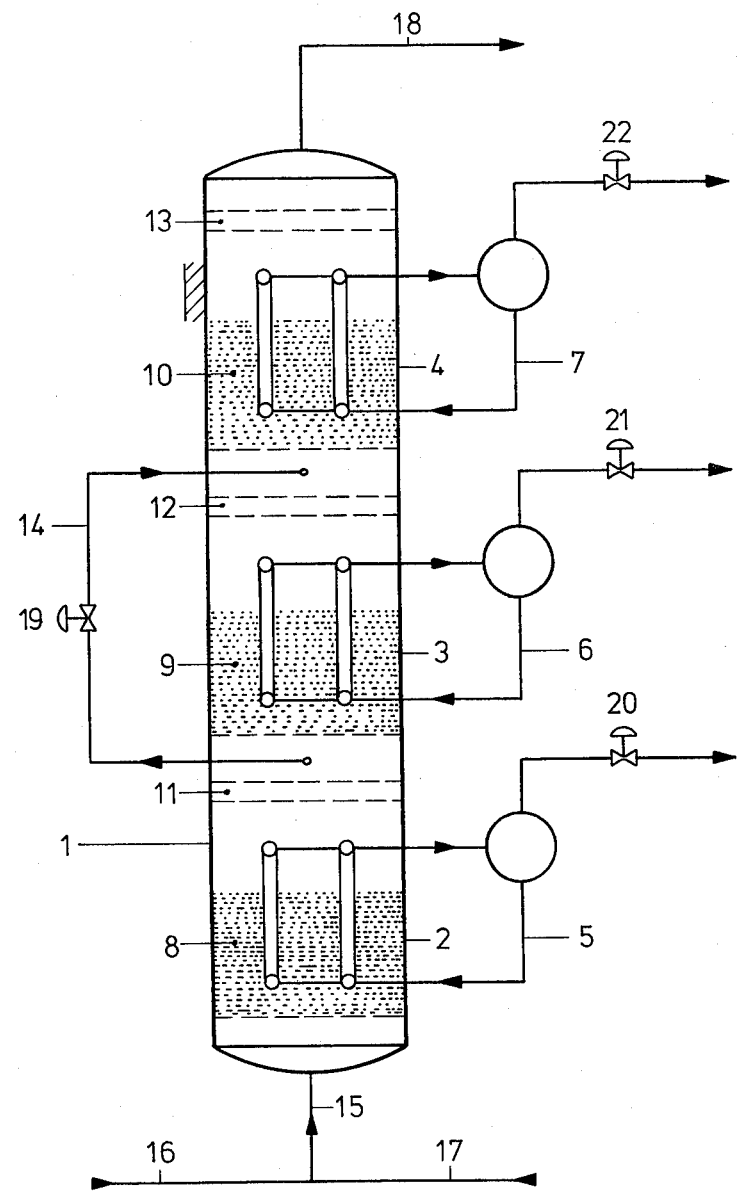

PROCESS AND APPARATUS FOR MULTI-STAGE CATALYTIC METHANIZATION OF GASES

This is a continuation of application Ser. No. 946,170, filed on Sept. 27, 1978, now abandoned.

This invention relates to processes and apparatus for the multi-stage catalytic methanisation of carbon monoxide-containing and hydrogen-containing gases at high pressure and temperature.

It is known that, from a primary gas such as a coal or coke oven gas, a gas resembling natural gas, i.e. a so-called SNG, may be produced by catalytic methanisation. This can be done in a wide variety of ways; for example a multi-stage process for the catalytic methanisation of coal gas at high pressure and temperature is described in German Offenlegungsschrift No. 1,545,470. In this process a mixture of coal gas and a carbon monoxide-rich gas and higher hydrocarbons is used as a feed gas. In the first process step, the hydrocarbons are hydrogenatingly cracked by means of a sulphur-resistant catalyst at a temperature exceeding 400° C. and a pressure of 5-50 bars gauge. The sulphur is converted to hydrogen sulphide and the carbon oxides are partly converted to methane. After separation of the hydrogen sulphide in an intermediate stage, the residual quantity of carbon monoxide, carbon dioxide and hydrogen is finally catalysed at a temperature below 400° to methane.

It is also known that feed gases having a high carbon monoxide content may first be treated in a converting stage with steam, in order partly to convert the carbon monoxide to carbon dioxide and hydrogen, and that a feed gas having a reduced carbon monoxide content may then be supplied to the subsequent methanisation. This process, however, requires a relatively high quantity of steam and operates satisfactorily only if the quantities of carbon monoxide and hydrogen in the feed gas are in a stoichiometrically correct ratio to each other.

Finally, a process is described in Offenlegungsschrift No. 2,449,587 for the simultaneous catalytic conversion and methanisation of a feed gas containing carbon monoxide, carbon dioxide, methane and hydrogen at a temperature of from 288° to 565° C. and a pressure of 35 to 140 bars gauge. This process avoids two separate process stages for the conversion and methanisation, but leads to difficulties in the removal of the reaction heat and the setting of the methane equilibrium.

The primary object of the present invention is to provide a methanisation process, which does not require a specific ratio of carbon monoxide to hydrogen in the feed gas and which operates even where there is an excess of carbon monoxide above the stoichiometric ratio. Furthermore, the process according to this invention requires less steam in the feed gas than is necessary with conventional conversion before methanisation.

It is a further object of the invention to provide an apparatus for carrying out the above process.

The present invention consists broadly in a process for the multi-stage catalytic methanisation of a carbon monoxide-containing and hydrogen-containing feed gas at high pressure and temperature, said process comprising the improved steps of premethanising said feed gas at a temperature of from 400° to 500° C., converting said premethanised gas and then finally methanising said converted gas at a temperature of from 300° to 380° C.

Thus in the process in accordance with the present invention, a conversion step is incorporated between two methanisation steps. This brings about the particular advantage that the steam which is produced in a considerable quantity in the premethanisation in the first process step as a consequence of the methanisation reactions:

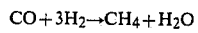

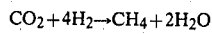

is consumed in the succeeding conversion step which entails the usual conversion reaction:

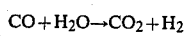

Consequently, the requirement for externally supplied steam, that is steam from a steam generator, is correspondingly reduced. Taking account of the quantities of steam produced in the methanisation reactions, the feed gas in the process of this invention needs to contain, for example, only 15% by volume of steam, without the stoichiometric ratio of carbon monoxide to hydrogen necessary for the conversion being thereby disturbed.

Preferably, the process of this invention operates at a pressure of 5 to 100 bar.

Since the final methanisation step also requires a stoichiometric equilibrium of carbon monoxide and hydrogen, reaction gas from the premethanisation step may be supplied to the gas leaving the conversion step before this gas enters the final methanisation step. The reaction gas from the premethanisation step possesses, since it is not yet converted, a relatively high carbon monoxide content and is therefore particularly suitable for setting the stoichiometric ratio of carbon monoxide to hydrogen in the reaction gas leaving the conversion step and entering the final methanisation step, since this reaction gas has a relatively high hydrogen content from the conversion reaction. The process of this invention is preferably carried out at a temperature of about 400° in the premethanisation step and a temperature of about 350° C. in the final methanisation step in order reliably to suppress decomposition of methane and the associated production of carbon on the methanisation catalyst. It is especially advantageous if the temperature in the conversion step is equal to that in the premethanisation step, since a temperature of about 400° C. is a favourable equilibrium temperature and moreover in this case the first two process steps can be operated with the same steam pressure on the cooling tube side.

Apparatus for carrying out the process in accordance with the invention, preferably comprises, in accordance with another aspect of the invention, a pressure reactor, means defining a first, premethanising zone in said reactor, means defining a second, conversion zone in said reactor adjacent said first zone, means defining a third, final methanisation zone in said reactor adjacent said second zone and remote from said first zone, a premethanising catalyst in said first zone, a conversion catalyst in said second zone, a final methanising catalyst in said third zone, means for supplying said feed gas and steam to said first zone, means for flowing reaction gas from said first zone to said second zone, means for flowing reaction gas from said second zone to said third zone and means for withdrawing product gas from said third zone.

A rapid course of reaction is assured if all three catalysts are formed into fluidized beds. The fluidized beds operate with usual catalysts, i.e. with nickel catalysts in the two methanisation zones and with an iron oxide-containing catalyst in the conversion zone. Preferably, however, the nickel catalyst in the final methanisation zone has a higher activity than the nickel catalyst in the premethanisation zone in order to assure a methane yield which is as high as possible.

The setting of the carbon monoxide content or the ratio of carbon monoxide to hydrogen for example to 1:3 in the reaction gas passing into the final methanisation step or zone from the conversion step or zone can be achieved in a very economical manner if a bypass line extends between the premethanisation zone and the final methanisation zone. This line supplies reaction gas having a relatively high carbon monoxide content from the premethanisation zone into the reaction gas leaving the conversion zone with a relatively low carbon monoxide content. The flow through the by-pass line is controlled by a valve.

In order to reduce carry-over losses and to ensure an undisturbed course of reaction, dust separators for removing entrained catalyst particles from the reaction gas are preferably situated between the individual zone and between the final methanisation zone and the product gas outlet from the pressure reactor.

Since the process of the invention takes place isothermally, cooling systems for removing the reaction heat are located in the individual reaction zones. Preferably these systems include cooling lines which pass through the reaction zones and lead to a steam generator. In this way, amongst other things, it is made possible to produce in the course of the process the steam necessary for the supply of the steam content in the feed gas.

The process and apparatus of the invention will now be described in more detail with reference to an example of the apparatus which is illustrated in the accompanying drawing which is a circuit diagram.

The apparatus comprises a pressure reactor 1 having three reaction zones 2, 3 and 4, each having a mutually independent cooling system 5, 6 and 7 respectively.

A premethanisation step takes place in the lowermost reaction zone 2. This reaction zone contains a fluidized bed 8 of a methanisation catalyst, for example a nickel catalyst having a relatively low nickel content. In the next zone, that is the middle reaction zone 3, there is a fluidised bed of a conversion catalyst 9, while the uppermost reaction zone 4 contains a fluidised bed of a methanisation catalyst, for example a nickel catalyst 10 having a relatively high nickel content. At the end of each reaction zone 2, 3, 4, there is a dust separator 11, 12, 13 respectively for removing entrained catalyst particles from the preceding reaction zone.

Between the premethanisation zone 2 and the final methanisation zone 4, a bypass line 14 extends and this by-passes the conversion zone 3. Carbon monoxide-containing reaction gas from the premethanisation zone 2 can be supplied to the reaction gas leaving the conversion zone 3 at the inlet to the zone 4 through the line 14. Pressure-regulated control valves 19, 20, 21 and 22 are located in the bypass line 14 and in the cooling systems 5, 6 and 7 respectively.

The pressure reactor 1 is supplied through a line 15 with feed gas, for example coal gas or coke oven gas, from a line 16, and with steam from a line 17. The product gas leaves the reactor 1 through a line 18 and is supplied, if desired after washing out of any entrained carbon dioxide and sulphur, to a gas storage unit.

The feed gas enters the reaction zone 2 at a temperature of about 200° C. and is isothermally premethanised there at a temperature of about 400° C. From the reaction zone 2, the reaction gas passes through the dust separator 11 into the reaction zone 3, in which the steam supplied through the line 17 and the steam produced in the reaction zone 2 is isothermally converted at a temperature of about 400° C. with carbon monoxide to carbon dioxide and consequently the carbon monoxide content is reduced. The reaction gas, which is isothermally converted in the reaction zone 5, passes through a dust separator 12 into the reaction zone 4. Depending upon the hydrogen content of this reaction gas, carbon monoxide-containing reaction gas from the reaction zone 2 is added to the reaction gas from the conversion zone 3 through the bypass line 14, in order to adjust the stoichiometric ratio of carbon monoxide to hydrogen for the final methanisation step.

In the reaction zone 4, the reaction gas is methanised at a temperature of about 350° C. and thereby the remaining carbon monoxide is reacted with hydrogen. The gas methanised in the final methanisation zone 4 consists essentially of methane, carbon dioxide and steam. This gas leaves the pressure reactor 1 through the dust separator 13 and the product gas line 18.

In a test, a feed gas at a pressure of 32 bar and with a set carbon dioxide content of the following analysis by volume was used:
2% Carbon Dioxide
29% Carbon Monoxide
53% Hydrogen
2% Nitrogen 0.13 m$^3$ of steam was added per 1 m$^3$ of feed gas. The gas was isothermally premethanised and converted at 400° C. in a pressure reactor of the type shown in the drawing and finally methanised at 350° C. The reaction gases from the individual reaction zones were analysed, with the result shown in the following table.

|  | Zone 1 (Vol. %) | Zone 2 (Vol. %) | Zone 3 (Vol. %) |
|---|---|---|---|
| $CO_2$ | 8.2 | 17 | 20 |
| CO | 20.4 | 7 | 0.02 |
| $H_2$ | 11.0 | 22 | 1.08 |
| $CH_4$ | 56.2 | 51.3 | 74.1 |
| $C_2$ | 0.2 | 0.2 | 0.3 |
| $N_2$ | 4.0 | 3.5 | 4.5 |

The data from the preceding table shows that, in the process of this invention, in spite of a very low flow rate of steam in the feed gas, a product gas having a carbon monoxide content of only 0.02% by volume is produced. Considered overall, the preceding gas analyses show how the composition of the feed gas changes through the three reaction zones to a product gas having a high methane content.

We claim:
1. A process for the isothermal multi-stage catalytic methanisation of a carbon-monoxide-containing and hydrogen-containing feed gas comprising the successive steps of
(a) isothermally reacting the feed gas in a fluidized bed to form a premethanised gas at a temperature of from 400° to 500° C.;
(b) subjecting the premethanised gas to a shift conversion under isothermal conditions, in a fluidized bed at about the same temperature; and
(c) methanising the converted gas in a fluidized bed under isothermal conditions, at a temperature of from 300° to 380° wherein the stoichiometric ratio of carbon monoxide to hydrogen in the converted gas is obtained by adding the premethanised gas thereto.

2. A process as claimed in claim 1, in which said high pressure at which said steps are carried out is from 5 to 100 bar.

3. A process as claimed in claim 1, further comprising the step of reacting steam produced in said premethanisation step with carbon monoxide in said conversion step.

4. A process as claimed in claim 1, wherein said premethanising step takes place at a temperature of about 400° C.

5. A process as claimed in claim 1 or claim 4, wherein said conversion step takes place at a temperature of about 400° C.

6. A process as claimed in claim 1, wherein said final methanisation step takes place at a temperature of about 350° C.

* * * * *

UNITED STATES PATENT OFFICE
CERTIFICATE OF CORRECTION

Patent No. 4,318,997  Dated March 9, 1982

Inventor(s) Claus Flockenhaus, et al

It is certified that error appears in the above-identified patent and that said Letters Patent are hereby corrected as shown below:

On the title page Item [75] should read:
[75]  Inventors: Claus Flockenhaus, Essen; Erich Hackler, Essen-Kettwig; Werner Lommerzheim, Mülheim/Ruhr, all of Fed. Rep. of Germany Signed and Sealed this Fifth Day of October 1982

[SEAL]

Attest:

Attesting Officer

GERALD J. MOSSINGHOFF

Commissioner of Patents and Trademarks